United States Patent [19]

Frings et al.

[11] Patent Number: 5,395,911
[45] Date of Patent: Mar. 7, 1995

[54] THERMALLY CURABLE MIXTURE CONTAINING EPOXY AND FORMAMIDE COMPOUNDS

[75] Inventors: Rainer B. Frings; Gerwald F. Grahe, both of Berlin, Germany

[73] Assignee: Dainippon Ink and Chemicals, Inc., Tokyo, Japan

[21] Appl. No.: 96,215

[22] Filed: Jul. 19, 1993

Related U.S. Application Data

[63] Continuation of Ser. No. 736,442, Jul. 29, 1991, abandoned.

[30] Foreign Application Priority Data

Jul. 30, 1990 [DE] Germany ............... 40 24 466.0

[51] Int. Cl.$^6$ ............................................. C08G 59/00
[52] U.S. Cl. ........................................ 528/87; 528/119; 528/88; 528/102; 528/103; 528/106; 528/111; 528/121
[58] Field of Search .............. 528/87, 88, 102, 103, 528/106, 111, 119, 121; 525/113

[56] References Cited

U.S. PATENT DOCUMENTS

| | | | |
|---|---|---|---|
| 3,538,050 | 11/1970 | Henderson . | |
| 4,203,900 | 5/1980 | Kaiser . | |
| 4,383,103 | 5/1983 | Kluger | 528/111 |
| 4,480,082 | 10/1984 | McLean et al. | 528/103 |
| 4,510,326 | 4/1985 | Lambert, Jr. et al. . | |
| 4,533,719 | 8/1985 | Waddill . | |
| 4,632,965 | 12/1986 | Hefner, Jr. . | |
| 4,668,757 | 5/1987 | Nichols | 528/99 |
| 4,833,204 | 5/1989 | Yusa et al. | 525/113 |
| 5,066,684 | 11/1991 | LeMay | 521/97 |

FOREIGN PATENT DOCUMENTS

| | | |
|---|---|---|
| 7900628 | 9/1979 | European Pat. Off. . |
| 0137074A1 | 4/1985 | European Pat. Off. . |
| 3246267A1 | 6/1983 | Germany . |
| 2058053 | 4/1981 | United Kingdom . |

OTHER PUBLICATIONS

WPIL, File Supplier, AN-89-030019, Derwent Publications Ltd., London, GB; & JP-A-63 305 969 (Hitachi Chemical K.K.) 13 Dec. 1988.
Patent Abstracts of Japan, vol. 6, No. 219 (C-132)(1097), 2nd Nov. 1982; & JP-A-57 121 026 (Tokyo Chibaura Denki) 28 Jul. 1992,
Derwent-Abstract 87-230 816/33 (JP 62 153 316), Dec. 27, 1985.
Derwent-Abstract 86-004 352/01 (JP 60 231 723), Mar. 29, 1984.
Derwent-Abstract 75 104 E/36 (JP 57 121 025), Jan. 20, 1981.
Derwent-Abstract 75 105 E/36 (JP 57 121 026), Jan. 21, 1981.
J. Chem. Soc. 1948, p. 1457.
Barkdoll, A. E. et al; J. Amer. Chem. Soc. 73, pp. 741–746 (1951).

*Primary Examiner*—Morton Foelak
*Assistant Examiner*—Richard Jones
*Attorney, Agent, or Firm*—Armstrong, Westerman, Hattori, McLeland & Naughton

[57] ABSTRACT

A thermally curable mixture contains 10–70% by weight of reactive compounds, 0.05–2% by weight of at least one basic catalyst, and at least one solvent. The reactive compounds are consisting essentially of a first reactive compound and a second reactive compound at a molar ratio between 1:1 and 1:10. The first reactive compound is a formamide selected from the group consisting of hydroxyformamides, di-formamides and poly-formamides, and the second reactive compound is at least one compound having an epoxy equivalent between 100 and 800 g KOH per mole epoxy group, selected from a group of aromatic di-glycidylethers and aromatic poly-glycidylethers. The basic catalyst is at least one chemical agent selected from the group consisting of tertiary ammonium salts, tertiary aromatic amines, and tertiary heterocyclic amines. The solvent is at least one chemical compound selected from the group consisting of aliphatic alcohols, ether alcohols, diether, and tertiary amides.

9 Claims, No Drawings

THERMALLY CURABLE MIXTURE CONTAINING EPOXY AND FORMAMIDE COMPOUNDS

This application is a continuation of application Ser. No. 07/736,442, filed Jul. 29, 1991, abandoned.

BACKGROUND OF THE INVENTION

1. Field of the Invention

The invention relates to thermally curable mixtures which consist of polyfunctional amides and aromatic di- or polyglycidylethers, or additionally a cyclic carbonate, and which are reacted by addition of a basic catalyst and are used as coatings or foams.

2. Related Art

Primary aliphatic and aromatic di- and polyamines have manifold uses as hardeners for epoxy coatings. It is especially advantageous that crosslinking takes place already at low temperatures between 0° and 100° C. and that because of the large choice of di- and polyamines of different chemical structure the properties of the finished coatings can be varied greatly. Disadvantageous, however, are the short pot-lives of such epoxy/amine-mixtures which reduce their storage stability and workability considerably, as well as the negative hygienic properties of many of the used amines. Also many amines show strong corrosive action, have a relatively high vapour-pressure and take up $CO_2$ readily from the air which reduces their solubility and reactivity against epoxy compounds.

Primary- and secondary amino-functions can be blocked in many ways chemically reversible, whereby the limitations named above can be avoided at least during the manufacture, storage and use of the coatings totally or partially.

One possibility for the reversible blocking is the reaction of primary and secondary amino groups with volatile organic and inorganic acids under salt formation. The release of the reactive amino-functions occurs by addition of aqueous bases in stoichiometric amounts relative to the amino content. This possibility can be used only in aqueous coating systems in which the released acids use up epoxy groups and corrode metallic substrates, however. Another possibility for the blocking of primary amino groups is the reaction with aldehydes and ketones under formation of aldimines and ketimines which are split hydrolytically to the starting products. The most blocking agents known from peptide synthesis have to be ruled out because of their high price and the deblocking methods unusual in coatings technology such as hydrogenation, photolysis or cleavage by aggressive reagents.

Acidic and basic hydrolysable groups are secondary or tertiary amido groups, preferably formamido groups. They can be prepared in many ways, e.g. by thermolysis or dehydration with hydroscopic agents of the respective ammonium salts, by reaction of the amines with CO under pressure and noble-metal-catalysis and by reaction of amines or ammonium salts with esters, preferably formic esters. These methods, such as e.g. the thermolysis and dehydration of ammonium salts and the amidation of esters in most cases are suitable only for amines without other reactive groups.

A blocking of primary and secondary amino-functions in compounds which have additionally other reactive groups such as OH—, SH— or ester-functions, is possible by carbonylation under pressure as described e.g. in the patents U.S. Pat. No. 4,510,326 and CS 183 083 or by reaction of ammoniumhydrochlorides with formic esters and triethylamine under acidic catalysis, as described by L. F. Tietze and Th. Eichler in the book "Reaktionen und Synthesen in organisch-chemischen Praktikum", page 120, G. Thieme Verlag, Stuttgart, New York, (1981), for aminoacidesters. The process named first requires, however, a very high technical expense, while the second process proceeds as a difficult controllable solid/liquid phase reaction, produces a large amount of non-usable triethylammoniumchloride and the final product, especially the hydroxyalkylformamide, can be separated hardly from the ammoniumchloride.

SUMMARY OF THE INVENTION

It is an object of the present invention to provide a thermally curable mixture in which crosslinkages form at a temperature between 100° and 200° C. to provide a film with good water resistance and good solvent resistance properties.

According to an aspect of the present invention the above-mentioned purpose is achieved by a thermally curable mixture which contains:

a) 10–70% by weight of reactive compounds, b) 0.05–2% by weight of at least one basic catalyst, and c) at least one solvent.

The reactive compounds consist essentially of a first reactive compound and a second reactive compound at a molar ratio between 1:1 and 1:10. The first reactive compound is a formamide selected from the group consisting of hydroxyformamides, di-formamides and polyformamides, and the second reactive compound is at least one compound having an epoxy equivalent between 100 and 800 g KOH per mole epoxy group, selected from a group of aromatic di-glycidylethers and aromatic polyglycidylethers.

The basic catalyst is at least one chemical agent selected from the group consisting of tertiary ammonium salts, tertiary aromatic amines and tertiary hetercocylic amines.

The solvent is at least one chemical compound selected from the group consisting of aliphatic alcohols, ether alcohols, diether, and tertiary amides.

DETAILED DESCRIPTION OF THE PREFERRED EMBODIMENT

It was found that hydroxyalkylformamide and aliphatic and aromatic diformamides crosslink in the temperature range between 100 and maximal 200° C. under basic catalysis fast with aromatic di- and polyglycidylethers based upon bisphenol-A or novolak which have an epoxy-equivalent between 100 to 800 g/mole epoxy group to give transparent, hard, but nevertheless flexible coatings of excellent water- and solvent-resistance. Especially advantageous for many applications seems the low water uptake, the good form stability and the very slight loss of hardness of these crosslinked films after water storage.

Especially effective proved to be β-hydroxyalkylformamides, such as e.g. 2-hydroxyethylformamide-1, 1-hydroxy-2-methyl-propylformamide-2, N-(N'-formylaminoethyl)-N-formyl-aminoethanol and N-formyl-aminodiethanol. Essential for the ability to crosslink with aromatic di- and polyglycidylethers seem to be OH-groups in β-position to the amido-groups.

Also diformamides, such as ethanediformamide-1.2, propanediformamide-1.3, hexamethylenediformamide- 1.6 and m-xylylenediformamide are very good crosslinkers for aromatic di- and polyglycidylethers.

Crosslinkable di- and polyformamides can be obtained also by reaction of mono- and dihydroxyalkylformamides with di- and polyisocyanates or with polyurethane-prepolymers having free NCO-groups in suitable solvents, such as ketones. Such products, the molecular weights of which can be between 300 and 2000 g/mole, stand out by an often better solubility in usual coating solvents and their mixtures. Since they can be manufactured in many combinations of di- and polyols, di- and polyamines with isocyanates, they are well suitable also for the modification of the working properties of the crosslinked materials to which they impart e.g. between adhesion and flexibility.

Suitable di- and polyisocyanates are e.g. hexamethylenediisocyanate, 2.4-toluylenediisocyanate, diphenylmethanediisocyanate, isophoronediisocyanate and their di- and trimerisation products. Suitable are also oligomeric and polymeric addition products of diols-, di- or polyamines, OH-functional polyacrylates and polyesters and the named di- and polyisocyanates, in which NCO-groups have to be retained which subsequently are reacted with mono- or dihydroxyalkylformamides to form amido-group-containing urethanes and polyurethanes.

Another class of di- and polyformamides contain ester groups and can be manufactured by reaction of mono- or dihydroxyakylformamides with di- or polycarbonic chlorides according to Schotten-Baumann or by transesterification with dicarbonic dialkylesters or polycarbonic esters, advantageously their methyl- or ethylesters. Also these products show an improved solubility in coating solvents and a better compatibility with aromatic epoxy resins.

Suitable dicarbonic dichlorides and diesters are derived e.g. from succinic-, maleic-, adipic-, sebacic acid, dodecane diacid, the isomeric phthalic acids, 1.3.5- and 1.2.4-benzenetricarbonic acids or pyromellitic acid.

Suitable as aromatic di- and polyglycidylethers are low molecular compounds with an epoxy-equivalent between 100 and 800 g/mole epoxide. Examples for these are bisphenol-A-diglycidylethers such as EP 139 or EP 140 (Reichhold Chemie AG, Hausen, Switzerland) and novalak-polyglycidylethers such as EPICLON 730 (DIC, Tokyo).

The mixture ratio of the reactive components necessary for a sufficient crosslinking is 1:1 to 1:10, favourably 1:1.5 to 1:4 and especially 1.5:2 moles epoxy groups per mole of reactive OH- or amide groups. Basic compounds such as quaternary ammonium hydroxides (e.g. tetramethylammoniumhydroxides, and especially advantageous trimethylbenzylammoniumhydroxide, quaternary ammoniumflorides, e.g. tetramethylammoniumfluoride, tertiary aromatic amines, such as benzyldimethylamine, N-heterocycles, such as N-methylimidazole and especially advantageous diazabicyclics, such as 1.4-diazabicyclo-(2.2.2.)-octane (DABCO), 1.8-diaza-(5.4.0)-undec-7-ene (DBU)) can serve as catalysts in amounts of 0.05 to 2% by weight, relative to the reactive components. Possibly additional co-catalysts, such as titanium-(IV)-esters, metal chelates or dialkyltinesters can be added in amounts of 0.05 to 2% by weight relative to the reactive components. Such compounds act catalytically for the crosslinking reaction and produce additional crosslinking sites in the coatings by reaction with the secondary OH-groups newly formed during crosslinking.

These non-compatible mixtures can be formulated with 20 to 45% by weight of solvent to clear, low-viscous coatings, the pot-life of which is several months, at least one month, however. Aliphatic, non-branched alcohols with 1 to 8 C-atoms, etherglycols, diether and tertiary formamides or their mixtures are possible as solvents. Named as examples are methanol, ethanol, isopropanol, n-butanol, i-butanol, butylglycol, methoxypropylglycol, diethylene-glycoldimethylether, N,N-dimethylformamide, N,N-dimethylacetamide and N-methylpyrrolidone. An especially advantageous solvent mixture consists of five parts n-butanol and three parts diethylene-glycoldimethylether or butylglycol. The components named above can be mixed without a large input of energy with simple stirrers to produce clear, thin coatings. Such coatings can be applied by known methods, such as dipping, brushing, rolling or spraying to many metallic substrates such as untreated and phosphated steel, tin plate and aluminum, glass, ceramics, paper and different surface-treated plastics, which are resistance and form-stable in the crosslinking temperature region of 100° to 200° C. and can be crosslinked at liquid coating layers up to 150 μm to transparent, hard and flexible films. The typical baking time for such thick liquid layers at 120° C. is 15 to 20 minutes.

Coatings, which contain quaternary ammoniumhydroxides or -fluorides as catalysts result after baking in glass-clear, colorless films whereas the films crosslinked with the aid of tertiary amines are colored slightly yellow.

The coatings prepared with the mixtures according to the invention contain small amounts of solvent, compared to conventional coatings with similar rheological properties. However, it seems desirable nonetheless to formulate coatings with still smaller amounts of solvents, preferably between 0 and 15% by weight.

Surprisingly it was found that cyclic carbonates such as ethylene-carbonate and especially advantageously propylenecarbonate are suitable reactive diluents for the thermal crosslinkable mixtures according to the invention. By addition of cyclic carbonates, preferably propylenecarbonate, the part of volatile solvents which are vapourized at the crosslinking temperatures between 100° and 200° C., can be reduced to 5 to 15% by weight in the coating. It could be proven by infrared spectroscopy of crosslinked films and by model studies with monofunctional formamides, cyclocarbonates and glycidylethers that the cyclocarbonates coreact in the crosslinking and are not remaining in the film as high-boiling solvents.

The mixture ratios of the three reactive components aromatic di- or polyglycidylether, cyclocarbonate and hydroxyalkylformamide or diformamide can be chosen in such a way that for each mole of epoxy group of the aromatic di- or polyglycidylether ¼ to 1 mole cyclocarbonate and ½ to 1 mole reactive OH- or amide group in the hydroxyalkylformamide or diformamide is available.

As catalysts, 0.05 to 2% by weight of the mentioned basic compounds from the classes of quaternary ammonium salts, tertiary amines and N-heterocyclics can be used.

As solvents, which are necessary with a weight portion of 5 to 15 weight % for the preparation of clear, at least one month storage stable coatings, mono- and difunctional alcohols with 1 to 8 C-atoms, preferably methanol-, n- and i-butanol and 1.2-propyleneglycol, etheralcohols, such as e.g. n-butylglycol and methoxypropanol, diethers, such as e.g. diethyleneglycoldimethylether, and tertiary amides such as e.g. N.N-dimethyformamide and N-methylpyrrolidone are to be considered.

While mixtures, which contain hydroxylakylformamides need only 5 to 8 weight % of low-boiling solvent for the preparation of clear coatings, coating mixtures based upon diformamides, preferably ethanediformamide-1.2, propanediformamide-1.2 and propanediformamide 1.3, require 10 to 15 weight % of low-boiling solvents for complete transparency of the coatings.

It can be done completely without an addition of low-volatile solvents for the compatibilisation of the crosslinkable mixtures if they contain hydroxylalkylformamides such as e.g. -hydroxy-ethylformamide, bis-(2-hydroxyethyl)-formamide or N-(N'-formylaminoethyl)-N-formyl-aminoethanol. In these cases the clear homogeneous mixtures can be obtained by addition of 5 to 10 weight % of a liquid aromatic mono-glycidylether, such as e.g. phenylglycidylether, o-cresyl-glycidylether, or p-tert.-butyl-phenylglycidylether, which crosslink in the same manner and under the same conditions.

Aliphatic and some aromatic diformamides, such as m-xylylene diformamide, are soluble in β-hydroxyethylformamide so that well usable crosslinking mixtures of these diformamide-hydroxyethyl-formamide-mixtures with aromatic mono-, di- and polyglycidylethers and cyclic carbonates, preferably propylenecarbonate, can be prepared in which the molar ratio of the reactive groups to each other has to correspond to the conditions mentioned above, namely between 1:1:1 and 1:5:5, preferably between 1:1:1 and 1:3:2 and especially 0.5–1:1:1:0.25–1 of reactive OH- or amide groups relative to the epoxy group and the cyclocarbonate.

Further it was found that the polyfunctional amides used in the curable mixtures can be prepared from numerous aliphatic, cycloaliphatic and aromatic compounds which contain primary and secondary aminofunctions and can have additionally hydroxyl-, thiol- or ester-groups, in aliphatic alcohols with 1 to 4 C-atoms with formic- and acetic esters of aliphatic alcohols with 1–4 C-atoms under retention of the other functional groups. In using aliphatic and cycloaliphatic compounds and formic esters, the amidation of the aminofunctions proceeds at temperatures between 0° to 80° C. very fast, complete and without additional catalyst. Amido alcohols, preferably formamido-alcohols, after amidation and removal of the alcohol and the excess of ester have a purity of more than 95%. The content of amidoalkylesters, determined by gas-chromatography, is always less than 1%, preferably below 0.3%. In contrast to this fact, in the usual method for the preparation of hydroxyalkylformamides from aminoalcohols and formic esters, as described in U.S. Pat. No. 4,203,900, always higher or lower amounts of formamidoesters are formed. By carrying out the reaction in the process according to the invention in short-chain alcohols, the equilibrium of the transesterification reaction is shifted to the left side of reaction scheme II

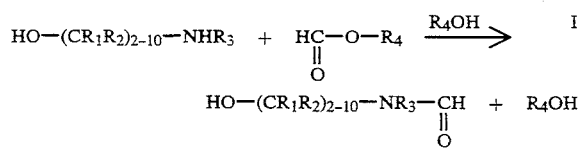

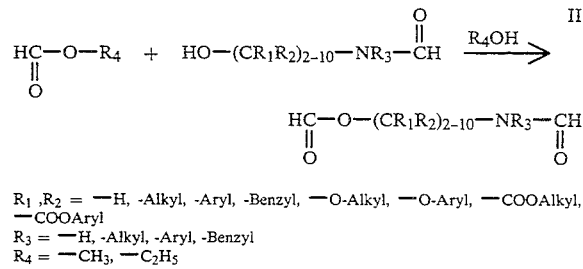

$R_1, R_2$ = —H, -Alkyl, -Aryl, -Benzyl, —O-Alkyl, —O-Aryl, —COOAlkyl, —COOAryl
$R_3$ = —H, -Alkyl, -Aryl, -Benzyl
$R_4$ = —CH$_3$, —C$_2$H$_5$ With the claimed process all sorts of primary and secondary amino alcohols of primary and secondary aliphatic and aromatic mono-, di- and polyamines can be formylated under mild conditions.

According to the claimed process, compounds with the following structures can be transformed into amides:

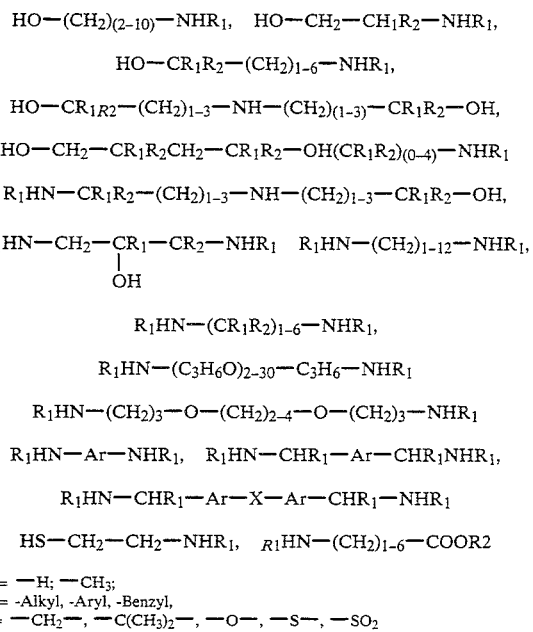

$R_1$ = —H; —CH$_3$;
$R_2$ = -Alkyl, -Aryl, -Benzyl,
$X$ = —CH$_2$—, —C(CH$_3$)$_2$—, —O—, —S—, —SO$_2$ Examples for compounds which can be amidated are:
Ethanolamine, N-methylethanolamine, propanolamine, isopropanolamine, diethanolamine, 2-amino-2-methyl-propanol-1, 2-amino-2-methyl-propandiol-1.3, 1.3-diamino-propanol-2, neopentanolamine, 2-(2-aminoethylamino)-ethanol, 2-aminoethanethiol, ethanediamine, 1.2-diaminopropane, 1.3-diaminopropane, 1.6-diaminohexane, isophoronediamine, diethylenetriamine, 1.3-bis-(aminomethyl)-cyclohexane, 4-aminomethyl-octanediamine-1.8, m-xyxlylenediamine, bis-(4-aminophenyl)methane, bis-(4-aminophenyl)-sulfone, β-glycine-ethylester.

While aliphatic and alicyclic amines and aminoalcohols can be formylated already at ambient temperature with formic esters, aromatic amines need higher temperatures up to 70° C. and a basic catalyst such as e.g. N-methylimidazole. The same reaction conditions are recommendable also for the acetylation of aliphatic amines and aminoalcohols with acetic esters.

In the amidation of the aliphatic and aromatic di- and polyamines the alcohol serves essentially as solvent for the starting and end products which are very well soluble in short-chain alcohols, especially in methanol. The claimed amidation process can be carried out especially advantageously if the alcohol used as solvent corresponds responds to the alcoholic component of the used ester, especially advantageously are methanol and ethanol. In this way the mixture remaining after isolation of the amidation products containing excess ester, alcohol and possibly unreacted amine can be used advantageously again for further amidation reactions. In many cases, the amides prepared by the process according to the invention, especially the formamides of short-chain amino-alcohols, need no further purification operations such as distillation or recrystallization.

Hydroxyalkylformamides and diformamides are versatile intermediates. They serve for the preparation of oxazolidinones and imidazolidinones as described in DE-OS 37 30 777 as well as for the synthesis of 2-oxazolines as described e.g. in EP-AS 0164 219 and in U.S. Pat. No. 4,203,900. These heterocycles are used e.g. as preproducts for pharmaceuticals, textile additives and stabilizers for plastics.

Other uses of hydroxyalkylformamides are known as well. They can serve as physiologically harmless humidifiers for cosmetics (K. Coupland, P. J. Smith, Spec. Chem., 6 (4), 10 ff. (1986), or for the impregnation of tire-cord made from nylon (U.S. Pat. No. 3,760,578). In JP 60/231724, the use of adducts of formamides and hydroxyalkyl-formamides in epoxy-compounds for the improvement of the tensile strength of amino-cured epoxy resins is described.

The thermally crosslinkable mixtures according to the invention consisting of $\beta$-hydroxyformamides, aliphatic or aromatic di- or polyformamides, aromatic di- or polyglycidylethers, cyclic carbonates and possibly additional aromatic monoglycidylethers and the coatings prepared therefrom have several extraordinary properties:

The mixtures consist exclusively of low-molecular compounds with their typical rheological properties such as low viscosity and good levelling on a large number of substrates.

Possibly other additives such as pigments, light stabilizers and other additives can be added to the mixtures.

The reactive, low-molecular components of these mixtures, however, in the temperature-range between 100° and 200° C. form a dense three-dimensional network with very good optical, mechanical and chemical properties.

The thermally crosslinkable mixtures have a lower content of volatile solvents in comparison to coatings based upon polymers with a similar workability. The solvent content can be reduced to 0–5 weight % so that the coating consists nearly exclusively of components with a low vapour-pressure which crosslink with each other. Nevertheless, these mixtures retain their viscosity at room-temperature for a longer period, at least for one month.

The cured coatings made from the thermally crosslinkable mixtures according to the invention are hard, nevertheless flexible, have a very good surface quality and adhesion to many different substrates, are hydrophobic and show a very good gloss and high transparency.

The chemical resistance against a large number of organic solvents is very good. They also have no tendency towards swelling. Especially remarkable is the observation that the hardness of the coatings is reduced only slightly after 24 hours storage in water as the water uptake of 80 to 100 μm thick films is below 5 weight %.

The loss of harness determined with a pendulum hardness tester according to KÖNIG (Erichsen GmbH, Hemer), according DIN 53 157, with starting values of 200 to 220 sec. is maximally 10% after 24 hours water storage with mixtures in which the crosslinking is catalyzed by tertiary amines. With mixtures catalyzed by ammonium salts, the loss of hardness is 30 to 50%.

The crosslinking of the mixtures according to the invention is based upon the formation of tertiary amino-, ether-, urethane-, urea- and oxazolidinone-, or in case of diformamide imidazolidinone-groups. The formation of urethane-, urea- and heterocyclic-crosslinking groups is responsible for the better flexibility, hardness and water storage stability compared to other epoxy coatings. Aliphatic, aromatic and arylaliphatic diformamides, such as ethanediformamide-1.2, hexamethylenediformamide-1.6 and m-xylylenediformamide are crystalline compounds with melting points above 80° C. They have a limited solubility only in very few solvents such as water, low alcohols and some solvents which are unsuitable for the coatings technology, such as dimethylformamide and N-methylpyrrolidone. They can be dispersed, however, in mixtures consisting of aromatic mono-, di- or polyglycidylethers and cyclic carbonates, especially propylenecarbonate, and basic catalysts resulting in low- to medium-viscous suspensions. The molar mixing ratios of the reactive components and the weight portions correspond to the ones of the coating mixtures named above. These suspensions are curable and can fill up open or closed forms well. At temperatures between 60° and 140° C., these mixtures in the form under split-off of CO and $CO_2$ result in hard, slightly yellow fine-porous foams which are solvent and water resistant. Gas generation and crosslinking start already at temperatures below the melting points of the diformamides. For the formation of these hard foams, preferably aromatic and arylaliphatic diformamides with a melting point between 80° and 250° C. such as those of m-xylylenediamine, bis-(4-aminophenyl)-methane and bis-(4-aminophenyl)-sulfone can be used.

The invention will be explained further with the following examples, it shall not be limited to these examples, however.

EXAMPLES

Example 1

1-hydroxyethylformamide-2

595.6 g (9.75 moles) ethanolamine 97% (Aldrich, Steinheim) were cooled in a 2-1 Erlenmeyer flask to 0 degrees Celsius in an ice bath, a mixture of 761.2 g methylformiate (=12.68 moles) and 443.2 g methanol was added during 2 hours. The temperature in the Erlenmeyer flask rose to 15 degrees Celsius. The reaction mixture was stirred over night at ambient temperature. Volatile compounds were distilled off in a rotary evaporator at 80 degrees Celsius and the light yellow product was fractionated over a 30 cm Vigreux column. The 1-hydroxyethylformamide-2 was distilled as a colourless liquid with a boiling point of 135–137 degrees Celsius/0.15 mbar.

Yield after distillation: 97% of theory. According to GC-analysis the fraction was >99% pure.

Example 2

1-hydroxy-2-methyl-propylformamide-2

178 g (=2.0 moles) 2-amino-2-methyl-propanol-1 (Aldrich, Steinhelm) were dissolved in 150 g methanol in a 1-1 flask equipped with a stirrer, a reflux condenser and a dropping funnel, a mixture of 117 g (=3.0 moles) methylformiate (Aldrich, Steinheim) in 300 g methanol was added during 2 hours so a slight reflux was obtained. Subsequently the mixture was stirred for an hour under reflux and the hot solution was concentrated with a rotary evaporator. Overnight a colourless crystallisate was formed, filtered off and dried under a vacuum oil pump for 12 hours. The purity according to GC was >97%.

Yield: 215 g 1-hydroxy-2-methyl-propylformamide-2=92% of theory, mp.: 68° C.

Example 3

Bis-(2-hydroxyethyl)-formamide=N-formylaminodiethanol 105 g (=1 mole) diethanolamie (Aldrich, Steinhelm) were dissolved in 100 g methanol in a 1-1 flask equipped with a stirrer, a reflux condenser and a dropping funnel, a mixture of 90 g (=1.5 moles) methylformiate (Aldrich, Steinheim) and 200 g methanol was added during 35 minutes. The temperature rose to 35 degrees Celsius. Subsequently the mixture was stirred for one hour under reflux and the hot solution was concentrated in a rotary evaporator. A slightly yellow, viscous liquid remained which according to gas chromatogram, mass spectrum and IR-spectrum consisted exclusively of bis-(2-hydroxyethyl)-formamide.

Yield: 62.3 g Bis-(2-hydroxyethyl)formamide=93.5% of theory.

Example 4

2-formamido-2-methylpropanediol 105 g (=1 mole) 2-amino-2-methylpropanediol-1.3 (Aldrich, Steinheim) were dissolved in 200 g methanol in a 1-1 flask equipped with a stirrer, a reflux condenser and a dropping funnel, a mixture of 90 g (=1.5 moles) methylformiate (Aldrich, Steinheim) and 100 g methanol was added during 40 minutes. The temperature rose to ca. 30 degrees Celsius. Subsequently the mixture was stirred for one hour under reflux and the hot solution was concentrated in a rotary evaporator. The residue was a slightly yellow, viscous liquid.

Yield: 132 g=100% of theory. Purity according to GC: >96%.

Example 5

N-methyl-N-formylaminoethanol 75 g (=1 mole) 2-methylaminoethanol were reached, as described in examples 1-4, with 90 g (=1.5 moles) methylformiate in 300 g methanol. After removal of the low boiling solvent a watery clear, low viscous liquid was obtained, which according to GC/MS-analysis and amine number determination was >99%.

Yield: 101 g=98% of theory.

Example 6

Hexamethylenediformamide-1.6

116.1 g (=1 mole) hexamethylenediamine (E. Merck, Darmstadt) were reacted, as described in examples 1-4, with 180 g (=3 moles) methylformiate in 300 g methanol. Subsequently the mixture was concentrated to dryness in a rotary evaporator and the product was recrystallized from methanol/acetone (3:1).

Yield: 165 g=96% of theory.

Purity according to GC:>99%, m.p.:107–108.5 degrees Celsius.

Example 7

Propanediformamide-1.3

148 g (=2 moles) propanediamine-1.3 (Aldrich, Steinheim) were formylated, as described in examples 1-4, with 150 g (=2.5 moles) methylformiate in 200 g methanol. The mixture was stirred for 2 hours, however under reflux. After removal of the boiling solvents a yellow, viscous liquid was obtained, which according to IR- and mass-spectra was the diformamide.

Yield: 250.4 g=96%.

Example 8

4.4′-diaformamidodiphenylmethane 50 g (=0.25 moles) 4.4′-diaminodiphenylmethane 95% (Aldrich, Steinheim) were dissolved in a mixture of 81 g (=1.1 moles) ethylformiate, 200 g ethanol, 0.5 g p-toluenesulfonic acid, added to the mixture and boiled for 5 hours under reflux. Thereafter no more amine bands were visible in the IR-spectrum. The hot solution was concentrated in a rotary evaporator. The obtained brown oil crystallized slowly. The product was taken up in methanol and crystallized as beige crystals. After two days thy were filtered off, washed with ethanol and dried under a vacuum water jet pump.

Yield: 54.3 g=86% of theory, 169–172 degrees Celsius.

Example 9

M-xylylenediformamide 35.6 g (=0.25 moles) m-xylylenediamine (Aldrich, Steinheim) were dissolved with 0.3 g p-toluenesulfonic acid in 75 g (1 mole) ethylformiate, 75 g ethanol and boiled for 2 hours under reflux. During the reaction a finely crystalline solid precipitated. After it has been cooled to 40 degrees Celsius the crystallisate was filtered off and dried at an ambient temperature under a vacuum water jet pump.

Yield: 43 g=89.5% of theory, mp: 128–129 degrees Celsius.

Examples 10

1-mercaptoethylformamide-2

38.5 g (=0.5 moles) mercaptoethylamine (Aldrich, Steinheim), 51.0 g (=0.69 moles) ethylformiate and 70 g ethanol were heated in 250 ml flask for 7 hours under reflux. Thereafter the amine was nearly completely reacted. Subsequently the solvents were removed in a rotary evaporator and a low viscous, reddish liquid remained which have purity of 94% according to GC.

Yield: 51.3 g=98% of theory.

Example 11

1-hydroxyethylacetamide-2

61.0 g (=1 mole) ethanolamine was added during one hour to a boiling mixture of 100 g (=1.35 moles) methylacetate, 150.7 g methanol, 0.1 g DABCO and boiled under reflux for 14 hours. Subsequently the solvents were removed in a rotary evaporator. The thus obtained N-acetylated product was a viscous, slightly yellow liquid which was pure according to GC.

Yield: 101 g=98% of theory.

Example 12

Isophorone-bis-(carbamatoethylformamide)

In a 500 ml flask, equipped with a magnetic stirrer and a reflux condenser, a mixture of 55.5 g (=0.25 moles) isophorone-diisocyanate (HUELS), 44.5 g (=0.5 moles) hydroxyethylformamide of example 1 and 150 G methylethylketone were heated with exclusion of humidity for 48 hours to 80 degrees Celsius. After 20 hours the mixture became homogeneous. The proceeding of the reaction was followed by NCO-titration (DIN 53185) and IR-spectroscopy (NCO: 220 cm$^{-1}$). When no more isocyanate could be detected, the solvent was distilled off in a rotary evaporator at a bath temperature of 50–80 degrees Celsius at 10 mbar vacuum as far as possible.

Yield: 103.2 g=100% of theory inclusive residual solvent.

The isophorone-bis-(carbamatoethylformamide) at ambient temperature was a highly viscous, slightly yellow liquid which was used for the coating experiments without further purification.

Example 13

In a 500 ml flask, equipped with a reflux condenser, a stirrer and a dropping funnel, 87.2 g (=0.5 moles) technical grade toluylenediisocyanate (TDI, BAYER AG) were dissolved in 180 g 1.4-dioxane and heated to 55 degrees Celsius with humidity exclusion. 33.4 g (=0.25 moles) 2-formamido-2-methylpropanediol-1.3 of example 4 were dissolved in 90 g dioxane and added during one hour. 2 hours after the last addition the titrade NCO-content was 5.2% (Theoretically 5.3%). 44.6 g (=0.5 moles) hydroxyethylformamide of example 1 was added during 15 minutes. After 16 hours no more free NCO-groups could be detected by IR-spectroscopy and titration. The solvent was distilled off in a rotary evaporator at a bath temperature of 80 degrees Celsius at 10 mbar vacuum as far as possible.

Yield: 170.4 g.

The addition product of 2 moles hyroxyethylformamide and 1 mole 2-formamido-2-methylpropanediol-1.3 to 2 moles TDI, a tri-functional formamide, was a solid amorphous mass, which at a temperature of 100 degrees Celsius became viscous. It was used for coating without further purification.

Example 14

Sebacoyldiethylformamide

In a 500 ml flask, equipped with a reflux condenser, a stirrer and a dropping funnel, 45.2 g (=0.51 moles) hydroxyethylformamide of example 1, 0.9 g 4-dimethylaminopyridine and 0.17 g p-toluenesulfonic acid, dissolved in a mixture of 52 g (=0.52 moles) triethylamine and 100 ml CHCl$_3$ (Merck, stabilized with amylene) were heated to 65 degrees Celsius with humidity exclusion, and a solution of 65.6 g sebacoylchloride (Aldrich, 97%) in 50 ml CHCl$_3$ was added during 3 hours. During the reaction triethylammonium-hydrochloride was precipitated. After totally 4 hours no acid-chloride-absorption (1799 cm$^{-1}$) could be detected by IR-spectroscopy. After being cooled to 0 degrees Celsius the salt was filtered off under vacuum. The mother liquor was concentrated to half in a rotary evaporator. From this solution further salt was precipitated in a refrigerator which was also filtered off. The two salt fractions were washed with 200 ml acetone, the washing solution was combined with the CHCl$_3$-filtrate and distilled in a rotary evaporator at bath temperature of 50 degrees Celsius under vacuum. A medium viscous, slightly yellow oil remained which could be without further purification.

Yield: 75.3=86.2% of theory sebacoyldiethylformamide of 95%.

The following examples 15a–29 show the results of the coating application tests and are summarized in table 1 and 2.

The coatings were applied with a 100 micro m spiral coater to panels of different materials such as glass, steel, aluminium and tin plate, and if not stated differently, baked for 20 minutes at 120 degrees Celsius or 15 minutes at 150 degrees Celsius. The pot-life of the coatings was at least one month in all cases.

Example 15a 11.3 g bisphenol-A-diglycidylether EPOTUF EP 139 (Reichhold AG, Hausen) and 1.45 g 2-hydroxyethylformamide-1 (see example 1) were dissolved under stirring in a mixture of 5 g n-butanol and 3 g diethyleneglycoldimethylether (diglyme) and mixed with 0.6 g of a 40% solution of trimethylbenzylammoniumhydroxide (E. Merck, Darmstadt). The part of non volatile components was 56.3% by weight. The homogeneous solution leveled very well on all tested substrates and resulted after being baked at temperatures between 120 to 150 degrees Celsius in hard, transparent and highly glossy films.

Example 15b

The coating has been the same composition as in 15a except the catalyst was replaced by 0.15 g 1.5-diazabicyclo-(4.3.0)-non-5-ene (DBN). After it had been baked, yellowish coloured, transparent and highly glossy films were obtained.

Example 16

10.2 EPOTUF EP 139 were dissolved together with 2.0 g 1-hydroxy-2-methyl propylformamide-2 (see example 2), stirred in a mixture of 5.8 g n-Butanol, 4.0 g diglyme and 0.6 g of a 40% solution of trimethylbenzylammoniumhydroxide. The part of non volatile components was 55% by weight. After being baked hard, transparent and highly glossy films were obtained.

Example 17

17.5 g novolak-polyglycidylether EPICLON 730S (DIC, Tokyo) and 2.5 g 2-hydroxyethylformamide-1 were dissolved and stirred in a mixture of 5.0 g n-butanol, 3.0 g diglyme and 0.2 g DBU were added. The part of non volatile components of this low viscous coatings mixture was 71% by weight. After being baked, scratch resistant, transparent and highly glossy, slightly yellow films were obtained.

Example 18

10.2 g Epotuf EP 139, 2.0 g bis-(2-hydroxyethyl)-formamide (see example 3) and 0.5 g trimethylbenzylammoniumhydroxide-solution were dissolved under stirring in a mixture of 5 g n-butanol and 4 g diglyme. The part of non volatile components was 57% by weight. The resulting colourless coatings showed the same good properties as in the examples above.

Example 19

11.3 EPOTUF 139, 2.2 g propanediformamide-1.3 (see example 7) and 0.2 g DBN were dissolved in 0.5 g n-butanol and 3.0 g diglyme and slightly stirred. The part of non volatile components was 63.1% by weight. After baking the result were, scratch resistant, yellow coating films with very good mechanical and optical properties.

Example 20

A mixture of 10.2 g EPOTUF EP 139, 2.6 g 2-formylamino-2-methylpropanediol-1.3 and 0.6 g 40% trimethylbenzylammoniumhydroxide solution were dissolved in 5.8 g n-butanol and 3.8 diglyme under stirring. The part of non volatile components was 56.6% by weight. Well crosslinking and solvent resistant coatings were obtained only at baking temperatures of at least 150 degrees Celsius.

Example 21

A mixture of 8.8 g EPOTUF EP 139, 2.6 g propylenecarbonate (Huels), 2.3 g 2-hydroxyethylformamide-1 and 0.7 g trimethylbenzylammonium-hydroxide-solution was dispersed with 3.4 g butylglycol. After it had been degassed, a clear, low viscous solution was produced which leveled very well on all tested substrates. After baking at 150 degrees Celsius for 15 minutes, hard, scratch resistant crosslinked coating films were obtained, which were transparent and highly glossy.

Example 22a

A mixture of 17.5 g EPOTUF EP 139. 5.2 g propylenecarbonate, 2.3 g 2-hydroxyethylformamide and 1.2 g 40% trimethylbenzylammonium-hydroxide-solution the solution was dispersed with 1.2 g n-butyldiglycol. After it had been degassed, the solution was clear and medium viscous. The part of non volatile components was 93% by weight. The coating was crosslinkable at 130 degrees Celsius within 15 minutes. The coating films were scratch resistant, highly glossy and transparent, leveled very well and were water and MEK resistant.

Example 22b

In the composition named in example 22a the catalyst was replaced with 0.3 g DBN and totally 1.5 g n-butyldiglycol were used. This solution became clear after 12–15 hours. The content of reactive compounds was 94.4% by weight. The coating films were yellowish and had properties comparable to the ones of example 15b. The decrease of pendulum hardness after 24 hours water immersion was considerably less.

Example 23

17.5 g EPOTUF EP 139, 5.2 g propylenecarbonate, 2.3 g 2-hydroxy-ethylformamide-1, 1.2 g 40% trimethylbenzylammoniumhydroxide-solution and 2.0 g phenylglycidylether were dispersed for 20 minutes. After 2 hours the solution became clear. The content of reactive compounds was 97% by weight. The coating films were baked at 130 and 150 degrees Celsius and had properties comparable to the ones of example 22a.

Example 23b

In the coating mixture according to example 23a the catalyst solution was replaced by 0.3 g DBN. After 5 hours of dispersing the coating became clear. The baked coatings were yellow and had properties similar to examples 22b and 23a.

Example 24

17.5 EPICLON 730 S, 5.5 g propylenecarbonate, 2.5 g 2-hydroxy-ethylformamide, 2.5 g phenylglycidylether and 0.2 g DBN were dispersed for 10 minutes. After 20 minutes the solution became clear. The coating films were baked at 130 and 150 degrees Celsius, were scratch resistant and only slightly yellow. They showed excellent solvent and water fastness.

Example 25

4.0 g of the isophorone-bis-(carbamatoethylformamide) from example 12 was mixed under stirring at 80 degrees Celsius with 2.0 g propylenecarbonate to a clear solution and dispersed subsequently with 7.0 g EPOTUF EP 139 and 0.2 g DBN for 10 minutes. After 2 hours the mixture was clear, baked on glass panels for 30 minutes at 120 degrees Celsius and 20 minutes at 140 degrees Celsius. The coatings were then slightly yellow.

Example 26

5.52 g triformamide from example 13 were dissolved in a mixture of 8.0 g diethyleneglycoldimethylether, 8 g EPOTUF EP 139 and 0.7 g trimethylbenzylammoniumhydroxide-solution (40% in methanol) were dispersed. After 3 hours the mixture was clear. Its content of reactive components was 51.8%. The medium Viscous coating was applied to glass panels, baked for one hour at 100 degrees Celsius and 30 minutes at 140 degrees Celsius. The coating films were partially irregular and had low gloss.

Example 27

4.82 g triformamide from example 13 were dissolved in a hot mixture of 6.0 g propylenecarbonate, 3.2 g DOWANOL PM (Dow Chemicals) and into this solution 10.5 EPOTUF EP 139 and 0.7 g trimethyl-benzylammoniumhydroxide-solution (405 in methanol) were dispersed. After 2 hours the mixture was clear. Its content of reactive components was 61.9%. The mixture was applied to glass panels, baked for 2 hours at 100 degrees Celsius, 1.5 hours at 120 degrees Celsius and one hour at 140 degrees Celsius. Only at 140 degrees Celsius sufficient crosslinking could be proved.

Example 28a 3.44 g sebacoyldiethylformamide from example 14 were dissolved in 2.0 g propylenecarbonate and dispersed with 7.0 g EPOTUF EP 139 and 0.4 g trimethylbenzylammoniumhydroxide-solution (40% in methanol). After one hour the mixture was clear, applied to glass panels, baked for an hour at 140 degrees Celsius, 1.5 hours at 150 degrees Celsius and one hour at 170 degrees Celsius. Whereas the coatings baked at 140 and 150 degrees Celsius were not or only slightly crosslinked, the coatings baked at 170 degrees Celsius showed a good solvent, water fastness, a high hardness and were colourless and glossy.

Example 28b

The mixture was prepared as in example 28a, the catalyst was replaced with 0.2 g DBN and the coatings were baked as in example 28a. Also these coatings were crosslinked only at 170 degrees Celsius and showed a slight yellowness.

Example 29

3.44 g sebacoyldiethylformamide, 7.0 g EPOTUF EP 139, 6 g propylenecarbonate and 0.5 g trimethylbenzylammoniumhydroxide-solution (405 in methanol) were dispersed together and applied to glass panels after degassing. Also these coatings were crosslinked sufficiently only at 170 degrees Celsius.

TABLE 1

Results of coatings tests with the baking enamels of examples 15a–29

| example | baking time (min)/-temperature (°C.) | substrate | surface assessment | gloss | scratch test | pendulum hardness (s) | resistance MEK | resistance H$_2$O |
|---|---|---|---|---|---|---|---|---|
| 15a | 20/120 | G1 | 1–2 | 1 | 2 | 241 | 75 | 75 |
|  |  | St | 1 | 1–2 | 1–2 | 238 | 75 | 75 |
|  | 10/150 | G1 | 1 | 1–2 | 1 | 217 | 75 | 75 |
|  |  | St | 1 | 1 | 1 | 232 | 75 | 75 |
| 15b | 20/130 | G1 | 2 | 1 | 1 | 178 | 75 | 75 |
|  |  | St | 1 | 1 | 2 | 231 | 75 | 75 |
|  | 10/150 | G1 | 1 | 1 | 2 | 195 | 75 | 75 |
|  |  | St | 1 | 1 | 1 | 239 | 75 | 75 |
| 16 | 20/120 | G1 | 1 | 1 | 1–2 | 228 | 75 | 75 |
|  |  | St | 1 | 1 | 1–2 | 228 | 75 | 75 |
| 17 | 20/130 | G1 | 1 | 1 | 1–2 | 230 | 75 | 75 |
|  |  | St | 1 | 1 | 1 | 232 | 75 | 75 |
|  | 10/150 | G1 | 1 | 1 | 1 | 225 | 75 | 75 |
|  |  | St | 1 | 1 | 1 | 235 | 75 | 75 |
| 18 | 20/120 | G1 | 1 | 1 | 1–2 | 237 | 75 | 75 |
|  |  | St | 1 | 1 | 1 | 241 | 75 | 75 |
| 19 | 20/130 | G1 | 2 | 1 | 1 | 242 | 75 | 75 |
|  | 10/150 | G1 | 1–2 | 1 | 1 | 242 | 75 | 75 |
| 20 | 50/120 | St | 1 | 1 | 4 | 203 | 10 | 50 |
|  | 10/150 | St | 1 | 1 | 1 | 230 | 75 | 75 |
| 21 | 15/130 | G1 | 4 | — | — | — | 5 | 0 |
|  | 15/150 | G1 | 1 | 1 | 1 | 216 | 75 | 75 |
| 22a | 15/130 | G1 | 1–2 | 1 | 2 | 211 | 75 | 75 |
|  | 15/150 | G1 | 1 | 1 | 1 | 213 | 75 | 75 |
| 22b | 15/130 | G1 | 1 | 1 | 1–2 | 213 | 75 | 75 |
|  | 10/150 | G1 | 1 | 1 | 1–2 | 213 | 75 | 75 |
| 23a | 20/130 | G1 | 1 | 1 | 1–2 | 220 | 75 | 75 |
|  | 10/150 | G1 | 1 | 1 | 1 | 220 | 75 | 75 |
|  | 20/130 | St | 3–4 | 1 | 3 | 227 | 75 | 75 |
|  | 10/150 | St | 1–2 | 1 | 1 | 237 | 75 | 75 |
| 23b | 20/130 | G1 | 3 | 1 | 2 | 227 | 75 | 75 |
|  | 10/150 | G1 | 3 | 1 | 1 | 221 | 75 | 75 |
|  | 20/130 | St | 3–4 | 1 | 3 | 199 | 25 | 50 |
|  | 10/150 | St | 3–4 | 1 | 3 | 235 | 75 | 75 |
| 24 | 20/130 | G1 | 1 | 1 | 1 | 227 | 75 | 75 |
|  | 10/150 | G1 | 1 | 1 | 1 | 225 | 75 | 75 |
|  | 20/130 | St | 2 | 2 | 2 | 219 | 75 | 75 |
|  | 10/150 | St | 1 | 1 | 2 | 224 | 75 | 75 |
| 25 | 30/120 | G1 | 2–3 | 1 | 3 | 192 | 15 | 75 |
|  | 20/140 | G1 | 2–3 | 1 | 2 | 193 | 75 | 75 |
| 26 | 60/100 | G1 | 3–4 | 3 | 1 | 230 | 20 | 75 |
|  | 30/140 | G1 | 2–3 | 2 | 1 | 222 | 75 | 75 |
| 27 | 3/140 | G1 | 3 | 3 | 1 | 234 | 75 | 75 |
| 28a | 90/150 | G1 | 1 | 1 | 4 | 3 | 15 | 40 |
|  | 90/170 | G1 | 1 | 1 | 2 | 196 | 75 | 75 |
| 28b | 90/150 | G1 | 1 | 1 | 3 | 14 | 15 | 75 |
|  | 90/170 | G1 | 1 | 1 | 1 | 210 | 75 | 75 |
| 29 | 90/150 | G1 | 1 | 1 | 4 | 6 | 10 | 60 |
|  | 90/170 | G1 | 1 | 1 | 2–3 | 130 | 75 | 75 | explanation:
assessment: 1 = excellent, 2 = good, 3 = fair, 4 = bad; pendulum hardness according to König (DIN 52157); solvent resistance determined by rubbing with MEK- or H$_2$O-soaked absorbent paper (double rubs); G1 = glass, St = untreated steel

TABLE 2

Change of pendulum hardness and surface assessment of baked enamel on glass after 24 hours storage in water at ambient temperature

| | | water storage (before) | | water storage (after) | |
|---|---|---|---|---|---|
| example | baking time (min)/-temperature (°C.) | surface assessment | pendulum hardness (s) | surface assessment | pendulum hardness (s) |
| 15 | 20/120 | 1–2 | 241 | 2 | 111 |
|  | 10/150 | 1 | 238 | 2 | 106 |
| 15b | 20/130 | 1 | 168 | 1 | 179 |
|  | 10/150 | 1 | 231 | 1 | 186 |
| 17 | 20/130 | 1 | 230 | 1 | 216 |
|  | 10/150 | 1 | 225 | 1 | 217 |
| 18 | 20/120 | 1 | 85 | 2–3 | 85 |
| 20 | 50/120 | 1 | 212 | 4 | — |

TABLE 2-continued

Change of pendulum hardness and surface assessment of baked enamel on glass after 24 hours storage in water at ambient temperature

| | | water storage | | | |
|---|---|---|---|---|---|
| | | (before) | | (after) | |
| example | baking time (min)/-temperature (°C.) | surface assessment | pendulum hardness (s) | surface assessment | pendulum hardness (s) |
| | 10/150 | 1 | 231 | 1 | 195 |
| 21 | 10/150 | 1 | 216 | 2–3 | 106 |
| 22a | 15/130 | 1 | 211 | 1 | 139 |
| | 10/150 | 1 | 213 | 1 | 148 |
| 22b | 20/130 | 1 | 213 | 1 | 207 |
| | 10/150 | 1 | 213 | 2 | 207 |
| 23a | 20/130 | 1 | 220 | 1–2 | 172 |
| | 10/150 | 1 | 220 | 1 | 214 |
| 23b | 20/130 | 2 | 227 | 2 | 214 |
| | 10/150 | 1 | 221 | 1 | 209 |
| 24 | 20/130 | 1 | 227 | 1 | 216 |
| | 10/150 | 1 | 225 | 1 | 217 |
| | 10/150 | 1 | 231 | 1 | 195 | explanation:
assessment: 1 = excellent, 2 = good, 3 = fair, 4 = bad; pendulum hardness according to König (DIN 52157)

What is claimed:

1. A thermally curable mixture consisting essentially of:
    a) 10–70% by weight of reactive compounds;
    b) 0.05–2% by weight of a basic catalyst; and
    c) a solvent;
    wherein said reactive compounds consist of a first reactive compound and a second reactive compound at a molar ratio between 1:1 and 1:10, said first reactive compound is a formamide selected from one of β-hydroxyformamides, di-formamides, and polyformamides, and said second reactive compound is a compound with an epoxy equivalent between 100 and 800 g KOH per mole epoxy group, selected from one of aromatic di-glycidylethers and aromatic poly-glycidylethers;
    said basic catalyst is at least one chemical agent selected from the group consisting of quaternary ammonium salts, tertiary aromatic amines and tertiary heterocyclic amines;
    said solvent is at least one chemical compound selected from the group consisting of aliphatic alcohols, ether alcohols, diether, and tertiary amides.

2. A thermally curable mixture consisting essentially of:
    a) 50–95% by weight of reactive compounds;
    b) 0.05–2% by weight of a basic catalyst; and
    c) a solvent,
    wherein said reactive compounds consist of a first reactive compound, a second reactive compound and a third reactive compound at a molar ratio between 1:1:1 and 1:5:5, said first reactive compound is a formamide selected from one of β-hydroxyformamides, di-formamides and polyformamides, and said second reactive compound is a compound with an epoxy equivalent between 100 and 800 g KOH per mole epoxy group, selected from one of aromatic di-glycidylethers and aromatic poly-glycidylethers, and said third reactive compound is at least one cyclic carbonate,
    said basic catalyst is at least one chemical agent selected from the group consisting of quaternary ammonium salts, tertiary aromatic amines, and tertiary heterocyclic amines,
    said solvent is a chemical compound selected from the group consisting of aliphatic alcohols, ether alcohols, diether, and tertiary amides.

3. A thermally curable mixture recited in claim 1, wherein said first reactive compound is formamide.

4. A thermally curable mixture recited in claim 1, wherein said catalyst is one of tertiary ammonium hydroxide and tertiary ammonium fluoride.

5. A thermally curable mixture recited in claim 1, wherein said molar ratio of the first reactive compound and the second reactive compound is between 1:1.5 and 1:4.

6. A thermally curable mixture recited in claim 2, wherein said third reactive compound is propylenecarbonate.

7. A thermally curable mixture recited in claim 2, wherein said molar ratio of the first reactive compound, the second reactive compound, and the third reactive compound is 1:3:2.

8. A thermally curable mixture consisting essentially of:
    a) a glycidylether selected from the group consisting of aromatic di-glycidylethers and aromatic poly-glycidylethers,
    b) a formamide selected from one of β-hydroxyformamides, di-formamides and polyformamides,
    c) a basic catalyst selected from the group consisting of quaternary ammonium salts, tertiary aromatic amines and tertiary heterocyclic amines, and
    d) a solvent.

9. A thermally curable mixture consisting essentially of:
    a) a glycidylether selected from the group consisting of aromatic di-glycidylethers and aromatic poly-glycidylethers,
    b) a formamide selected from one of β-hydroxyformamides, di-formamides and polyformamides,
    c) a basic catalyst selected from the group consisting of quaternary ammonium salts, tertiary aromatic amines and tertiary heterocylic amines,
    d) a solvent, and
    e) a cyclic carbonate.

* * * * *